United States Patent [19]

Mallo

[11] Patent Number: 5,147,921
[45] Date of Patent: Sep. 15, 1992

[54] NEW POWDERED SUPERABSORBENTS, CONTAINING SILICA, THEIR PREPARATION PROCESS AND THEIR USE

[75] Inventor: Paul Mallo, Chatou, France

[73] Assignee: Societe Francaise Hoechst, Puteaus, France

[21] Appl. No.: 720,648

[22] Filed: Jun. 25, 1991

[30] Foreign Application Priority Data

Aug. 14, 1990 [FR] France .................. 90 10338

[51] Int. Cl.$^5$ .................. C08K 3/36; C08L 33/02
[52] U.S. Cl. .................. 524/493; 524/492; 524/556; 524/847; 524/832; 524/833
[58] Field of Search ............... 524/492, 493, 556, 847, 524/832, 833

[56] References Cited

U.S. PATENT DOCUMENTS 4,499,217  2/1985  Yoshimura et al. ................. 524/492

FOREIGN PATENT DOCUMENTS 0187306  11/1982  Japan .................. 524/556

OTHER PUBLICATIONS

WPIL, File Supplier, AN-88=288718, Derwent Publications Ltd.
WPIL, File Supplier, AN-85=253475, Derwent Publications Ltd. Patent Abstracts of Japan, vol. 8, No. 19.

Primary Examiner—Paul R. Michl
Assistant Examiner—Peter Szekely
Attorney, Agent, or Firm—Remy J. VanOphem

[57] ABSTRACT

Hydrophilic, powdered superabsorbents which are insoluble in water, containing by weight, in the dry state, in combination, from 1 to 45% of colloidal silica with an average diameter of non-agglomerated particles of about 9 to about 50 nanometers and 99 to 55% of a cross-linked polymer based on free acrylic acid, partially or totally salified by a sodium or potassium, preparation process and use notably for the absorption of aqueous fluids.

7 Claims, No Drawings

NEW POWDERED SUPERABSORBENTS, CONTAINING SILICA, THEIR PREPARATION PROCESS AND THEIR USE

BACKGROUND OF THE INVENTION

In the field of superabsorbents, designated hereafter as SAP, cross-linked hydrophilic powdered polymers which are insoluble in water, based on free acrylic acid, partially or totally salified by an alkali metal are currently used.

These polymers are generally obtained by grinding polymer gels which have been chopped up and dried, these polymer gels being the product of a polymerization reaction in an aqueous solution of free acrylic acid, partially or totally salified by an alkali metal. It is known that these polymerization reactions in aqueous solution are carried out in a quasi adiabatic fashion starting with aqueous solutions with low monomer concentrations (about 10 to 25%) in such a manner as to be able to control the exothermic reaction. At the end of polymerization, polymer gels are obtained which are swollen with all the water used in the polymerization reaction and must be dried in order to be able to convert them into powder.

The handling of these water-swollen gels is laborious and delicate for they are soft and viscous, and their drying and then their grinding is more onerous the more water they contain.

In order to obviate these inconveniences, the Applicant has discovered new cross-linked, hydrophilic, powdered superabsorbents which are insoluble in water, based on silica and free acrylic acid polymers, partially or totally salified by an alkali metal.

SUMMARY OF THE INVENTION

Within the scope of the present invention, by alkali metal is designated sodium or potassium and by silica, colloidal silica, in a state of non-agglomerated elementary particles of an average diameter of about 9 to about 50 nanometers.

The products according to the present invention are characterized by the fact that they contain by weight, in the dry state, and in combination, from 1 to 45% of silica and from 99 to 55% of a cross-linked polymer based on free acrylic acid, partially or totally salified by an alkali metal, preferably sodium or potassium.

Notably a subject of the invention is the products as defined above characterized in that they contain by weight, in the dry state, and in combination, from 10 to 40% of silica and from 90 to 60% of a cross-linked acrylic acid-alkali metal acrylate polymer, preferably sodium or potassium, containing in molar proportions from 10 to 50% of acrylic acid units.

Among the latter products, a more particular subject of the invention is the products as defined above characterized in that they contain by weight, in the dry state and in combination, from 10 to 40% of colloidal silica, the particles of which have an average diameter of 20 to 50 nm and from 90 to 60% of a cross-linked acrylic acid-sodium or potassium acrylate copolymer containing in molar proportions from 15 to 35% acrylic acid units.

The polymers present in the present invention are cross-linked preferably with a monomer or several diethylene monomers which are soluble in water such as bisacrylamidoacetic acid or diallyloxyacetic acid or one of their alkali metal or ammonium salts. The quantity of cross-linking monomers used can vary greatly, but usually from 0.05 to 0.5 mmole of cross-linking monomers per mole of free or salified acrylic acid employed, are used.

The products of the present invention are powdered, insoluble in water, hydrophilic and water-swellable. They contain little or no residual monomers. Their water absorption capacity, determined according to the test T1 described hereafter, is greater than 200 g per g of dry product, their salt water absorption capacity at 9 g of sodium chloride per liter, determined according to test T2 described hereafter, is greater than 25 g per g of dry product.

According to test T1, 0.5 g of test product in 500 g of water is agitated for 30 minutes at 20° C., then the gel obtained is weighed after allowing it to drain. The found weight is taken to 1 g of dry product. According to test T2, 2 g of test product in 500 g of an aqueous solution of sodium chloride at 9 g per liter is agitated for 30 minutes at 20° C., then the gel obtained is weighed after allowing it to drain. The found weight is taken to 1 g of dry product.

The products of the present invention are not a simple mixture of colloidal silica and a cross-linked polymer based on free acrylic acid, partially or totally salified by an alkali metal, but a real combination of silica and the polymer. The water-swollen gels obtained with the products of the invention are firm, do not stick together and are easy to handle unlike the water-swollen gels obtained with products of the prior art, which are soft and viscous. The fact that with the products of the invention firm and non-sticking water swollen gels are obtained is extremely interesting from an industrial and application point of view, for on the one hand the products of the invention can be easily obtained by a polymerization process in aqueous solution, and on the other hand, the products of the invention have water and salt water absorption capacities which are approximately identical to those shown by products of the prior art while containing less organic material.

Also the present invention relates to a process for obtaining the products defined above characterized in that the colloidal silica and the free acrylic acid, partially or totally salified by an alkali metal are polymerized in water, as a mixture, in the presence of a hydrosoluble cross-linking monomer and a hydrosoluble polymerization initiator, then the water-swollen polymer gel thus obtained is dried to a water content of less than 10% by weight and finally ground into powder.

The process is preferably carried out in an inert atmosphere in water containing, by weight, 1 to 20% of colloidal silica and, in the dissolved state, from 5 to 25% of free acrylic acid, partially or totally salified by an alkali metal as well as the desired quantity of cross-linking monomer.

The polymerization initiators used are the hydrosoluble initiators currently used for the polymerization in aqueous solution of acrylic acid partially or totally salified by an alkali metal. There can be notably cited the redox systems of alkali metal or ammonium persulphate - alkali metal or ammonium bisulphite or disulphite or sulphite. Advantageously the redox system sodium persulphate - sodium disulphite is used. The cross-linking monomer chosen will be preferably bisacrylamidoacetic acid or diallyloxyacetic acid.

The polymerization reaction is started by the slow and progressive introduction of an aqueous solution of the chosen initiator into the agitated and carefully de-oxygenated reaction medium. When the initiator system is a redox pair, an aqueous solution of each constituent of this pair is preferably introduced successively into a reaction medium. The polymerization is generally initiated at a temperature of between 20° and 40° C., then it is preferably conducted in a quasi adiabatic manner. From the initiation, the reaction medium gels progressively so well that it cannot be agitated. At the end of the exothermic reaction the reaction medium is kept at a temperature of 40° to 60° C. for 30 minutes to 3 hours. In this way a non-sticking water-swollen gel is obtained, with a good mechanical behavior which can be taken from the polymerization reactor, then dried in a ventilated oven at a temperature lower than 80° C. The polymerization yield is quantitative and the product isolated after drying is a white, solid, crumbly material which can be easily reduced to a fine powder. Advantageously, the gel is chopped up or extruded as it leaves the polymerization reactor, before being dried, then ground. A product in the form of a white powder having the desired granulometry free of residual monomers and insoluble in water, is obtained.

The polymers according to the invention have useful properties for absorbing aqueous fluids: notably they show a strong absorption power for aqueous solutions containing hydrosoluble mineral salts, as well as alkali or alkaline-earth metal salts and they are capable of absorbing relatively large quantities of sea water. They also find remarkable uses in the manufacture of certain articles of hygiene, notably intended for the retention of urine.

DETAILED DESCRIPTION OF THE PREFERRED EMBODIMENT

The following examples illustrate the invention without however limiting it.

EXAMPLE 1

An aqueous phase is prepared under agitation and at ambient temperature, containing:
108 g (1.5 mole) of acrylic acid,
0.325 g (0.6 mmole) of sodium diethylenetriamine-pentaacetate, (DTPANa),
0.0546 g (0.276 mmole) of bisacrylamidoacetic acid (ABAA),
463.65 g of water containing in solution 60.6 g (1.08 mole) of potassium hydroxide,
80 g of a commercial silica sol containing, by weight, 50% water and 50% colloidal silica, the non-agglomerated particles of which have an average diameter of 50 nm.

This aqueous phase is then placed in a polymerization reactor, then it is carefully de-oxygenated by bubbling through nitrogen and finally it is heated to 40° C. under agitation, in an inert atmosphere.

At this temperature, the following are introduced successively, a solution of 0.08 g (0.336 mmole) of sodium persulphate dissolved in 10 g of water over 5 minutes, then a solution of 0.06 g (0.316 mmole) of sodium disulphite dissolved in 10 g of water over 10 minutes.

At this stage, the weight of the aqueous phase is about 672 g and it contains, by weight, 22.2% of monomers, 5.9% of silica and about 71.8% of water. The proportion of cross-linking monomer is 0.092 mmole per one mole of monomer and the initiation of the polymerization reaction is carried out with 0.225 mmole of sodium persulphate per mole of monomer and 0.210 mmole of sodium disulphite per mole of monomer.

After initiation, an exothermic reaction develops immediately and the reaction medium gels progressively. Agitation is stopped and the reaction medium is left for 3 hours at 40°–45° C. in an inert atmosphere.

Then, after cooling the reaction medium to 20° C., the polymer gel is isolated, chopped up and finally dried in a ventilated oven at 80° C. for 15 hours. The product obtained is then ground into a fine powder.

In this way 189 g of a white powder containing 5.2% water is obtained. This product contains by weight, in the dry state, 21.15% silica and 78.85% of a cross-linked acrylic acid - potassium acrylate copolymer, 28-72 in molar proportions.

In the tests T1 and T2, this product shows respectively a water absorption capacity of 248 g/g and a salt water absorption capacity of 34 g/g.

EXAMPLES 2-3

Operating under the same conditions as in Example 1, starting with 1.5 mole of acrylic acid neutralized to 72% with potassium hydroxide, and preserving/retaining a monomer concentration of 22.2% in the aqueous phase and the same quantities in molar proportions of initiator, the following products are prepared, noted in table 1 by varying on the one hand the quantities of silica, and on the other, the quantities of cross-linking monomer.

EXAMPLE 4

An aqueous phase is prepared under agitation and at ambient temperature containing:
108 g (1.5 mole) of acrylic acid,
0.325 g (0.6 mmole) of sodium diethylenetriamine-pentaacetate, (DTPANa),
0.0546 g (0.276 mmole) of bisacrylamidoacetic acid (ABBA),
303 g of water,
80 g of a commercial silica sol containing by weight 50% water and 50% colloidal silica the non-agglomerated particles of which have an average diameter of 50 nm.

This aqueous phase is then placed in a polymerization reactor, then it is carefully de-oxygenated by bubbling through nitrogen and finally it is heated to 45° C. under agitation in an inert atmosphere.

At this temperature the following are introduced successively, a solution of 0.08 g (0.336 mmole) of sodium persulphate dissolved in 10 g of water over 5 minutes, then a solution of 0.06 g (0.316 mmole) of sodium disulphite dissolved in 10 g of water over 10 minutes.

At this stage the weight of the aqueous phase is about 519 g and it contains by weight 20.8% of monomers, 7.7% of silica and about 71.5% of water. The proportion of cross-linking monomers is 0.814 mmole per one mole of monomer and the initiation of the reaction is carried out with 0.225 mmole of sodium persulphate per mole of monomer and 0.0210 mmole of sodium disulphite per mole of monomer.

After initiation, an exothermic reaction develops immediately and the reaction medium gels progressively. Agitation is stopped and the reaction medium is left for 3 hours at 40°–45° C. in an inert atmosphere, Then, after cooling the reaction medium to 20° C., the polymer gel is isolated and chopped up. This is then replaced in a polymerization reactor. Then an aqueous solution of 60.6 g (1.08 mole) of potash dissolved in 600 g water is added very slowly and under agitation. Then the whole is left under agitation for 8 hours in such a way as to ensure that the neutralization is homogeneous.

The polymer gel is then dried at 80° C. in a ventilated oven for 15 hours, then it is ground.

In tests 1 and 2, this product shows a water absorption capacity of 80 g/g and a salt water absorption capacity of 40 g/g.

COMPARATIVE EXAMPLE A

An aqueous phase is prepared as in Example 1 containing:
129.71 g (1.8 mole) of acrylic acid,
0.39 g (50.72 mmole) of DTPA, Na,
0.0656 g (0.332 mmole) of ABAA,
701.8 g of water containing in solution 76.72 g (1.37 mole) of potassium hydroxide.

This aqueous phase is then placed in a polymerization reactor, then it is carefully de-oxygenated by bubbling through nitrogen and finally it is heated to 40° C. under agitation in an inert atmosphere. At this temperature, the following are introduced successively under agitation, a solution of 0.096 g (0.403 mmole) of sodium persulphate in 10 g of water over 5 minutes, then a solution of 0.072 g (0.379 mmole) of sodium disulphite in 10 g of water over 10 minutes.

The reaction medium is then treated as in Example 1. In this way a product free from silica is obtained, the characteristics of which are given in Table 1.

COMPARATIVE EXAMPLE B

An aqueous phase is prepared under agitation and at ambient temperature containing:
108 g (1.5 mole) of acrylic acid,
0.325 g (0.6 mmole) of sodium diethylenetriaminepentaacetate (DTPA Na),
0.0273 g (0.138 mmole) of bisacrylamidoacetic acid (ABBA),
503.65 g of water containing in solution 60.6 g (1.08 mole) of potassium hydroxide.

40 g of powdered silica having an average particle diameter of 10 micrometers is then added. The silica cannot be dispersed in the reaction medium despite very vigorous agitation. After 3 days of vigorous agitation, the silica is still not dispersed in the reaction medium. The test was then abandoned.

COMPARATIVE EXAMPLE C 7.9 g of polymer prepared as in Comparative Example B and 2.1 g of powdered silica, having an average particle diameter of 10 micrometers, are mixed together dry in a mortar.

In tests 1 and 2, this product shows a water absorption capacity of 138 g/g and a salt water absorption capacity of 14 g/g.

TABLE 1

| Ex | Co | NP | PCM | Cs | W | D.E. | H$_2$O | T1 | T2 |
|---|---|---|---|---|---|---|---|---|---|
| 1 | 22.2 | 72 | 184 | 21.2 | 189 | 94.8 | 2.5 | 248 | 34 |
| 2 | 22.2 | 72 | 184 | 10 | 166 | 95.0 | 3.0 | 294 | 39 |
| 3 | 22.2 | 72 | 184 | 35.0 | 229 | 95.7 | 1.9 | 323 | 35.5 |
| 4 | 20.8 | 72 | 184 | 21.2 | — | 95.0 | — | 80 | 40 |
| A | 22.2 | 72 | 184 | 0 | 189 | 92.6 | 3.4 | 216 | 36.4 |
| B | — | — | — | — | — | — | — | — | — |
| C | 22.2 | 72 | 184 | 21.2 |  | 95 |  | 138 | 14 |

Co: concentration of monomers in the reaction medium expressed as percentage by weight.

NP: Proportion of neutralization of acrylic acid expressed as molar percentage.
PCM: Proportion of cross-linking monomers expressed as mmoles per 1,000 moles of monomers.
Cs: Concentration of silica in the final product expressed as percentage by weight.
D.E.: Dry extract of isolated product expressed as percentage by weight.
H$_2$O: Weight of water eliminated per gram of final product expressed in grams.
W: Weight of the isolated product expressed in grams Examination of Table 1 shows that the products of the present invention have water and salt water absorption properties which are identical or even superior to the same product free from silica. Consequently, for an identical weight of polymer, the products of the present invention have clearly improved water and salt water absorption capacities.

I claim:

1. Hydrophilic powdered superabsorbents which are insoluble in water, comprising by weight in the dry state, from about 1 to about 45% of colloidal silica wherein non-agglomerated particles of said colloidal silica have an average diameter of about 9 to about 50 nanometers, and from about 99 to about 55% of a cross-linked polymer based on free acrylic acid wherein at least a portion of said acrylic acid is salified by sodium or potassium.

2. Hydrophilic powdered superabsorbents according to claim 1, comprising by weight in the dry state, from about 10 to about 40% of said colloidal silica, and from about 90 to about 60% of said cross-liked polymer, said cross-linked polymer comprising acrylic acid and an acrylate chosen from the group consisting of sodium acrylate or potassium acrylate, and said cross-linked polymer containing in molar proportions from about 10 to about 50% of acrylic acid units.

3. Hydrophilic powdered superabsorbents according to claim 1 comprising by weight in the dry state, from about 10 to about 40% of said colloidal silica wherein non-agglomerated particles of said colloidal silica have an average diameter of about 20 to about 50 nanometers, and about 90 to about 60% of said cross-linked polymer, said cross-linked polymer comprising acrylic acid and an acrylate chosen from the group consisting of sodium acrylate or potassium acrylate, and said cross-linked polymer containing in molar proportions from about 15 to about 35% of acrylic acid units.

4. Process for forming hydrophilic powdered superabsorbents according to claim 1 comprising the steps of:
polymerizing in water said colloidal silica and said free acrylic acid, wherein said free acrylic acid is at least partially salified by sodium or potassium, in the presence of a hydrosoluble cross-linking monomer and a hydrosoluble polymerization initiator, so as to produce a water-swollen gel;
drying said water-swollen gel sufficiently to produce a dried polymer gel having a water content of less than 10% by weight; and
grinding said dried polymer gel to a powder.

5. Process for forming hydrophilic powdered superabsorbents according to claim 4 wherein said cross-linking monomer is bisacrylamidoacetic acid.

6. Process for forming hydrophilic powdered superabsorbents according to claim 4 wherein said cross-linking monomer is diallyloxyacetic acid.

7. Process for forming hydrophilic powdered superabsorbents according to claim 4 wherein said polymerization step occurs quasi-adiabatically.

* * * * *